United States Patent

Böcker et al.

[11] Patent Number: 5,997,561
[45] Date of Patent: Dec. 7, 1999

[54] SKIN CUTTER FOR PAINLESS EXTRACTION OF SMALL BLOOD AMOUNTS

[75] Inventors: Dirk Böcker, Heidelberg; Heinrich Fruhstorfer, Marburg, both of Germany

[73] Assignee: Roche Diagnostics GmbH, Mannheim, Germany

[21] Appl. No.: 09/117,527
[22] PCT Filed: Feb. 4, 1997
[86] PCT No.: PCT/EP97/00501
    § 371 Date: Jan. 25, 1999
    § 102(e) Date: Jan. 25, 1999
[87] PCT Pub. No.: WO97/28741
    PCT Pub. Date: Aug. 14, 1997

[30] Foreign Application Priority Data

Feb. 6, 1996 [DE] Germany .......................... 196 04 156

[51] Int. Cl.⁶ .................................................. A61B 17/32
[52] U.S. Cl. ........................................... 606/182; 606/181
[58] Field of Search ..................... 606/181, 178, 606/182, 185; 128/770

[56] References Cited

U.S. PATENT DOCUMENTS

| 4,750,489 | 6/1988 | Berkman et al. | 606/181 |
| 5,318,584 | 6/1994 | Lange et al. | 606/181 |
| 5,613,978 | 3/1997 | Harding | 606/181 |

*Primary Examiner*—Michael Buiz
*Assistant Examiner*—Kevin Truong
*Attorney, Agent, or Firm*—Nikaido, Marmelstein, Murray & Oram LLP

[57] ABSTRACT

Cutting device for skin obtaining small blood samples from human or animal tissue in an almost pain-free manner. A blade (13) is made to oscillate by an oscillator (14, 32) and is lowered into the tissue and again retracted at a relatively slow speed. In a first embodiment, the blade oscillates essentially parallel to the cutting edge of the blade and the tissue surface. In a second embodiment, the blade oscillates essentially perpendicular to the tissue surface. An advantage of the device of the reduced pain during pricking.

31 Claims, 5 Drawing Sheets

Fig. 1

Epidermis

Corium

Fig. 2

Epidermis

Corium

SKIN CUTTER FOR PAINLESS EXTRACTION OF SMALL BLOOD AMOUNTS

The present invention addresses a device for cutting skin to obtain small blood samples from human or animal tissue in an almost pain-free manner. It comprises a blade with a cutting edge having a length of less than 10 mm and an oscillator to make the blade oscillate essentially parallel to the cutting edge.

To take small amounts of blood from the finger or the earlobe for diagnostic purposes, one uses lancets which are pricked into the corresponding body part either manually or with the aid of a simple apparatus by the doctor or lab personnel. It is a matter of fact that the lancet has to be sharp and sterile. Otherwise, there are no particularly high demands to be met by the doctors' offices as blood samples are collected from individual patients in greater time intervals and the procedure is carried out by specially trained staff.

The requirements are significantly higher when blood lancet devices are used which are to be operated by the patient. They are necessary to allow patient groups that are at a particular risk to regularly determine certain analytical blood values by home monitoring.

This applies in particular to diabetics who regularly and frequently have to monitor their blood glucose level to keep it within certain levels by adjusting the amount of insulin to be injected which depends on food intake, physical activity, and other factors. This is of utmost importance for the health of these patients to avoid delayed serious damage such as blindness and amputation of body parts.

For this reason, one has developed easy to handle and relatively inexpensive analytical systems which usually comprise blood test strips and a corresponding evaluation instrument. Although the possibility of performing an easy and relatively inexpensive analysis is available to every patient today, the self-monitoring of blood glucose levels has still not reached the desired general acceptance among diabetics. The main reason being the pain that accompanies the pricking procedure when taking the blood sample.

Prior art knows lancet devices where a spring-propelled lancet pricks the tissue at a very high speed. Blood emerges from the so-created wound which can then be used for diagnostic purposes. Devices of this kind are known, for example from U.S. patents U.S. Pat. No. 4,203,446 and U.S. Pat. No. 4,895,147. There is a great variety of such devices with differently ground lancets and different spring mechanisms available on the market. Experiments have shown, however, that the pain caused by this kind of device cannot be lowered under a limit which the user clearly identifies as being unpleasant. What makes it even more difficult in the case of diabetics is that the test must be carried out frequently; the affected skin parts such as the finger tips and earlobes develop cornifications which in turn require deeper penetration levels thus causing more pain during pricking.

Numerous different blood lancet devices have been developed that are suitable to generate the wound necessary to collect the blood specimen in a simple and relatively pain-free manner. Examples are described in patents U.S. Pat. No. 4,442,836, U.S. Pat. No. 4,469,110, U.S. Pat. No. 4,535,769, and U.S. Pat. No. 4,924,897. Blood sampling device for driving a lancet and lancets are made to match one another and are also referred to as blood collection systems. Despite some progress, the pain caused by the cutting procedure when using blood lancet device designed for patient use is still too great.

The pain sensed during cutting could be reduced in blood lancet devices where the needle is guided in a controlled manner (U.S. Pat. No. 4,824,879 and U.S. Pat. No. 5,318,584). The devices of this kind are known as controlled guidance systems, as opposed to ballistic systems where the lancet, propelled by a spring, contacts the skin surface in a relatively uncontrolled manner.

It was, hence, an object of the present invention to propose a device which causes less pain during blood sampling as is the case with prior arts systems. It was another object of the invention to provide a blood lancet where the penetration depth can be reproduced in a more precise and improved manner than is the case with known devices.

The object was accomplished in accordance with the invention in that the skin is penetrated in a manner where there is no pressure wave directed perpendicular to the skin and where a relatively small amount of pain receptors is activated due to precise guidance and a relatively small penetration depth of the lancet/blade. This can be achieved in that the skin is penetrated/opened in a procedure that is carried out essentially parallel to the skin surface. This cutting procedure causes significantly less pain than pricking.

In accordance with the invention, the pain sensed when obtaining small amounts of blood is reduced in that a rapid oscillating movement is superimposed on the movement (usually a linear movement) of the blade that is necessary to enter the tissue. The excursion of the blade generated by this oscillating movement can principally be transverse to the tissue or essentially perpendicular to the tissue. With respect to these two embodiments, two different blade types have proven to be expedient so that the embodiments are described separately hereinafter.

When coupling a slow pricking movement with an oscillating movement, it is advantageous that despite an extremely high relative movement of the blade with respect to the skin, a pressure wave affecting deeper layers of the blade is almost completely avoided since the excursion of the blade is very small despite the high speed (preferably ranging around 10–200 $\mu$m) and there is virtually no pressure component being generated perpendicular to the tissue surface. The blade "falls" into the skin. The penetration principle is, hence, based on a cutting procedure which can be carried out by an "oscillating" blade without a significant pressure component running perpendicular to the direction of movement. Owing to the small stroke of the blade, the cut is limited to very small dimensions and, hence, easy to control.

Coupling a slow blade movement with an oscillating movement leads to cutting procedures which cause less pain than do the methods for obtaining small blood samples known from prior art.

Time-consuming tests have shown that the disadvantages of the blood lancets known in prior art are likely due to the painfullness of the skin penetration process which is essentially caused by the activation of pain receptors and their afferent signals. When the lancet arrives on the tissue a pressure wave is generated that propagates predominantly in the direction of movement. This pressure wave precedes the moving blade and thus activates additional pain receptors which would not be activated during penetration and cutting if the lancet would execute a mere cutting and ripping process. Avoiding a pressure wave when the lancet hits the skin can, hence, significantly reduce the pain sensation. Moreover, the undefined penetration depth and the uncontrolled movements of the lancet are likely to be additional reasons for unnecessary high pain sensation when using known systems.

The device of the invention can be further improved when the skin opening is kept as small as possible, preferably smaller than 1.5 mm, more preferably smaller than 1 mm, and when the cutting movement is carried out in a controlled manner.

It is also important that the site opening be generated in a controlled movement and not in an uncontrolled "rip". Ripping the tissue would lead to a corresponding pressure wave and/or pulling of the tissue which then causes pain. Advantageous movements are those where the blade is guided such that forward and backward movements are uniform. It is also advantageous to control the movement such that the forward movement upon reaching a predefined dead point changes into a backward movement.

The following figures are given to describe the invention in greater detail.

Figure 10:
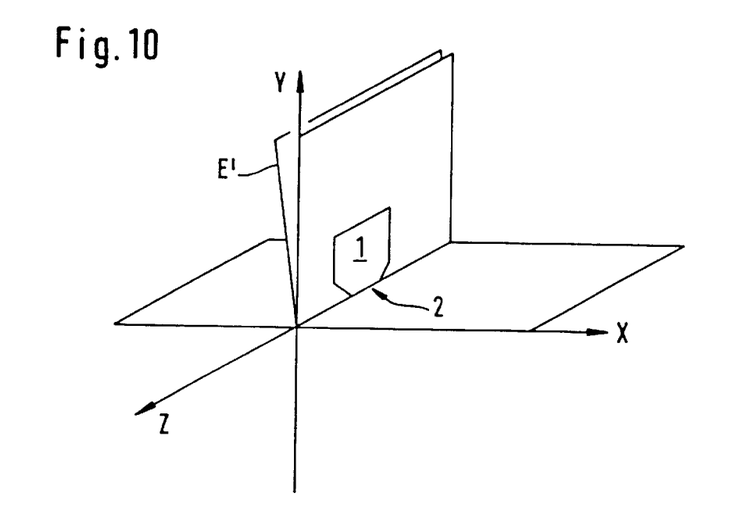
FIG. 10: System of coordinates for defining directions of movement

In order to define the directions of movement of the lancet, FIG. 10 shows a system of coordinates. The tissue surface is located in the XZ-plane. In order to penetrate the tissue, the lancet must carry out a movement with a Y-component, i.e. a movement having a component perpendicular to the tissue surface. In the case shown here, the cutting edge (2) is located on the Z-axis while the blade (1) is located within the XY-plane. The blade can now be guided perpendicularly, i.e. in direction of the negative Y-axis, into the tissue; or it can be moved in a plane E' which is tilted with respect to the XY-plane. The description "essentially perpendicular to the tissue surface" when used with respect to the direction of movement should also include movements which are tilted by, e.g. 30°, with respect to the XY-plane. In a first embodiment the blade is made to oscillate transversely to the direction of movement. In the system of coordinates of FIG. 10, this is an oscillating movement of the blade in direction Z.

The present invention is further directed to a process for obtaining small volumes of blood by a process where an oscillating blade is being moved in direction towards the tissue to be penetrated, is being lowered into the tissue in a direction primarily vertical to the skin surface and is being retracted out of the tissue. This can be accomplished by an active movement of the blade in direction towards the tissue as well as by an active movement of the tissue. Furthermore it is not necessary that the blade is already in oscillation while contacting the tissue surface. It is also possible to start oscillation of the blade after contact between blade and tissue has been established.

In almost all parts of its body, the human being possesses epithelial skin where blood sampling with lancets is not possible at all or very difficult as this type of skin, owing to its high retraction properties, will close immediately after pricking or cutting so that the blood emerging from the blood vessels cannot reach the surface of the skin or is released into subcutaneous tissue parts causing microhematomas. Skin parts that are suitable for obtaining blood samples include the tips of fingers and toes and the earlobes. On his finger and toe tips the human being possesses ridged skin. The top layer of this skin is the epidermis with a thickness of 0.1 to 0.5 mm. Below the epidermis is the corium consisting of the stratum papillare and the stratum reticulare. Below the corium is the subcutis. The upper part of the corium and the stratum papillare are of particular importance for obtaining small amounts of blood in almost pain-free manner. The stratum papillare features a finely woven net of blood vessels and pain receptors located closely together. In this part of the tissue the blood vessels can be divided into capillaries and microvessels. Capillaries are shaped like hair needles reflected in the papillae of the skin. Arterial blood rises from the inside of the tissue to the curvature in the hair needle to release oxygen to the surrounding tissue; it is then via the venous system conducted back into deeper layers of tissue in the form of venous blood. Within the present invention it has been found that due to anatomic properties, it suffices to penetrate the epidermis and cut open a few hair needle-like blood vessels of the papillary layer and/or cut open a few microvessels located in this region of the tissue to obtain an amount of blood that is sufficient to satisfy the diagnostic purpose (appr. 5 μl–30 μl).

Figure 1:
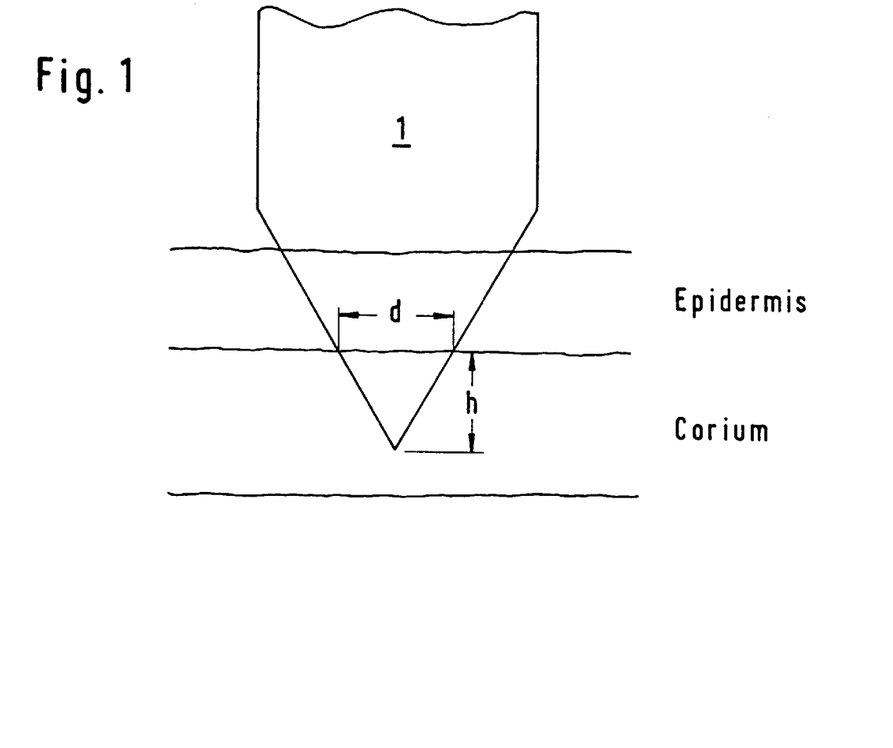
FIG. 1: Principal interaction between penetration depth and cutting width when using pointed lancets

Prior art lancets, however, penetrate the corium much deeper and in an uncontrolled manner, i.e. with heavy movements perpendicular to the propelling direction. The reason for this can be understood from FIG. 1. In order to generate a wound of width d on the surface of the corium, the tip of the lancet must enter the corium at a depth h. With the technology known from prior art, this depth h can only be reduced when a lancet with a flatter tip is selected, i.e. reducing the h/d-ratio. More blunt lancets, however, cause more pain during pricking as was shown in experiments.

The First Embodiment (Vampire)

In accordance with the invention, the pricking pain is reduced in that the blade is made to oscillate a high rate while the oscillating blade is lowered into the tissue are relatively slow speed, preferably slower than 2 km/h. In a first embodiment of the invention, the blade is oscillated essentially parallel to the cutting edge.

Figure 2:
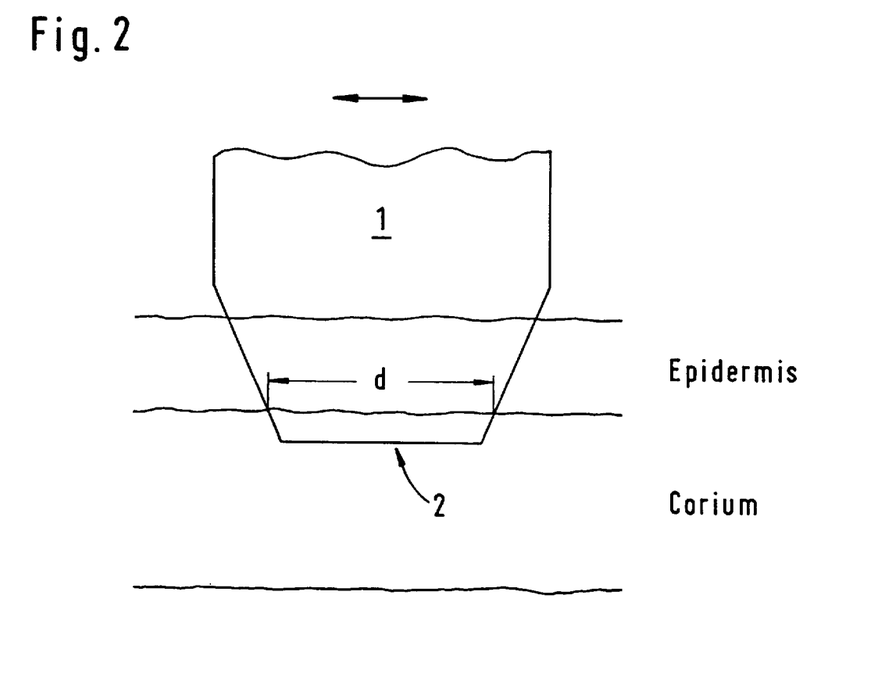
FIG. 2: Arrangement of blade and tissue with respect to one another

FIG. 2 shows the principal arrangement of blade and tissue. The blade (1) shown has a cutting edge (2) which executes an oscillating movement in direction toward the double arrow shown in the figure. When the blade, while oscillating, approaches the epidermis, it is capable of penetrating it without causing significant pain. Due to the oscillating movement, the epidermis is then cut open; as compared to currently available pricking lancets, it is now possible to lower the blade into epidermis and corium at a much slower speed. From FIG. 2 it can be seen that this embodiment uses a blade type where a sufficiently wide piece d of the tissue is cut open while the penetration depth of the corium remains very small. Owing to the arrangement of the hair-needle-like blood vessels and other microvessels found in this region within the corium, said vessels are effectively cut open by the oscillating movement of the blade. A cutting width d of 300 to 900 μm is already sufficient in order to obtain a sufficient amount of blood. For obtaining larger amounts of blood it is in accordance with the invention of course also possible to use correspondingly longer blades.

The Oscillator

In order to allow the blade to enter the tissue in an almost pain-free manner, experience has shown it to be important that the blade oscillate essentially parallel to the cutting edge at frequency above 500 Hz. The cutting device in accordance with the invention could further be significantly improved by raising the oscillation frequency to above 700 Hz. Particularly efficient cutting is achieved with frequencies in the kilo-Herz range or above 900 Hz. Pain sensation during cutting is significantly influenced by the oscillation amplitude. Experiments have shown that the amplitude should be below 500 µm. A preferred amplitude is one below 300 µm, particularly preferred below 250 µm. Oscillators to implement the described requirements include in particular piezo elements, ultrasonic ceramics, electrodynamical transformers as well as mechanical transformers. Piezo elements have proven particularly well as oscillators which execute changes in length upon application of an electrical voltage. As these changes usually amount to only one or a few µm, it is necessary to have a mechanical transformation to achieve larger amplitudes. This can be accomplished by a piezo element coupled to one end of a bar and a blade coupled to the other end. The bar should have a low weight in order to minimize a damping of the oscillation. The bar is preferably made of a ridgid material in order to achieve a proper energy transfer from the oscillator onto the blade. Bar and piezo element are properly coupled to a mass. It is, however, also possible to advantageously use a stack of piezo elements where the changes in length of the individual elements are added up.

Mechanical transformers which lead to an oscillation of the blade are so called spring-mass-oscillators, which can be accomplished with a tuning fork, for example, at the one arm of which there is attached the blade or a device to hold the blade. It has shown to be particularly useful to operate the oscillator at a resonance frequency since the amplitude of the blade is high under such conditions.

The Blade

Blades with a cutting edge of less than 10 mm have proven to be suitable for cutting devices designed to obtained small blood samples. Cutting edges with a length between 0.2 to 2 mm, preferably 0.4 to 1.5 mm have proven to be suitable for obtaining blood samples ranging around 100 µl. Cutting edges of 0.5 to 1.0 mm in length are particularly suitable.

Materials such as steel that are commonly used in prior art lancets haven proven well for the blades. Generally, it is also possible to use metals, glasses, ceramic materials and plastics. Particularly well suited are plastics which can be processed by injection molding and which are ridgid enough after cooling down. When using suitable injection molding forms a separate process step for sharpening the blade can be avoided. Experiments have shown it to be advantageous to coat the blades with substances which reduce friction between blade and tissue. By reducing the friction between blade and tissue, it is possible to avoid the transfer of mechanical energy into the tissue and, hence, pain caused by heat. In a particularly preferred embodiment bar and blade are a mechanical unit which can be exchanged. In the medical field it is desirable due to hygienic reasons to have a disposable unit which can be exchanged after each cutting process. Bar and blade can be made from different materials, however, it is preferred that both are made from the same material.

The Manually Operated Blood Lancet

Figure 3:
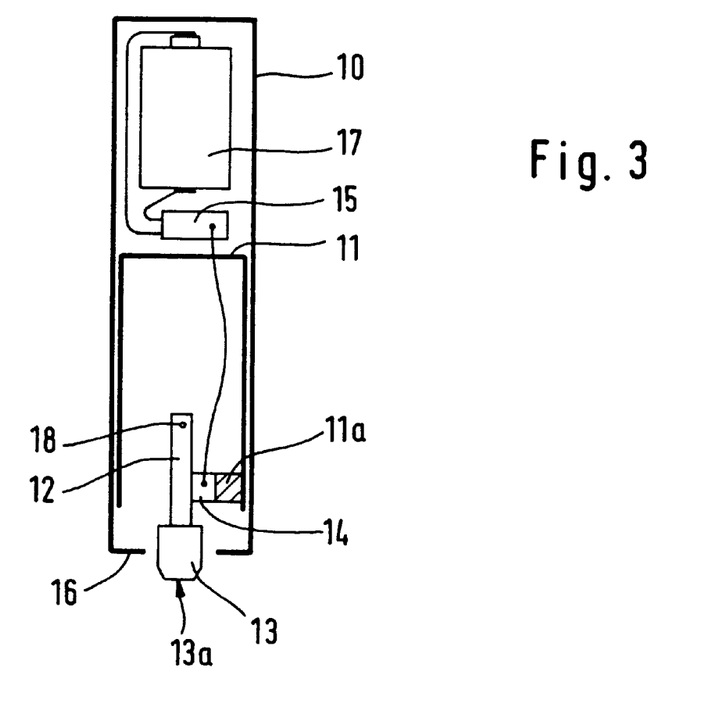
FIG. 3: Manually operated vampire blood lancet

FIG. 3 shows a blood lancet in accordance with the invention. Said lancet comprises a housing containing the blade and the oscillator. The housing has an outer cover (10) which serves to handle the device. Inside the cover there is a bar (12) to which the blade (13) is attached. A piezo crystal (14) connected to bar (12) is activated via an electronic oscillation generator (15) such that blade (13) executes oscillating movements essentially parallel to the cutting edge (13a). In the example shown here, another cover (11) is located inside the outer cover (10) where it can be moved such that the portion of the blade which projects out of the outer cover (10) can be adjusted. An axis (18) connects bar (12) with cover (11) such that this end of the bar is attached to a mass. At its bottom end, cover (10) is provided with a contact surface (16) which is manually placed onto the tissue. The portion by which the blade projects beyond the contact surface, hence, defines the depth of the cut in the tissue. The invention proposes that the cutting devices feature an adjusting unit to define the maximum and minimum distances by which the blade can project beyond the contact surface. The adjusting range of this interval is preferably selected such that its lower limit is longer than 200 µm while its upper limit is smaller than 2500 µm. This adjusting range is preferably set between 0.5 and 2.0 mm or, even more preferred, between 0.7 and 1.3 mm.

For proper performance of the device it is important that the bar (12) be made of a material that exhibits a sufficiently high modulus of elasticity to transfer the energy of the piezo oscillation to the blade (13). Suitable materials for the bar are, for example, glass, spring steel, plastics and ceramics. Moreover, it is also important that the weight of the oscillating components (bar and blade) is small in comparison to the weight on the opposite site of the piezo element. In FIG. 3 the piezo element is coupled via a connecting piece (11a) to the inner cover (11). It is particularly advantageous to operate the apparatus such that bar and blade oscillate at resonance frequency.

The Spring-Operated Blood Lancet

Figure 4:
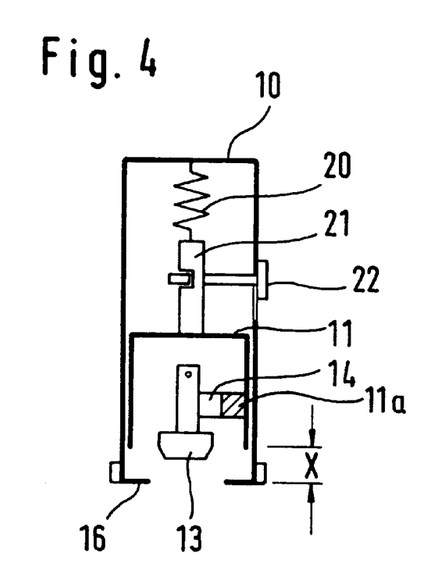
FIG. 4: Blood lancet with spring as propelling mechanism

FIG. 4 shows examples of embodiments where the manual movement which is necessary with the apparatus shown in FIG. 3, is replaced by the effect of a spring element (20). Spring (20) is connected to guide rail (21) which has a recess for a lever (22) to engage. Lever (22) is provided with a push-button located outside the housing. When pressing the push-button, the lock is released and the inner cover (11) is moved relative to the outer cover. Blade (13) is thus moved outside the outer cover. By varying the distance X between the edge of the inner cover (11) and the inside of the contact surface (16) in the initial position, it is possible to adjust the cutting depth by which the blade penetrates the tissue. This can be accomplished, for example, by varying the length of the outer cover, e.g. with the aid of a screw. Additional options to vary the penetration depth are known from U.S. Pat. No. 4,895,147 and U.S. Pat. No. 5,318,584. The arrangement can also be selected such that the blade is fixed in its position while the skin contact surface is provided on the front side of a cover which is mounted to an adjustable abutment in a spring-supported manner.

The unit for adjusting the penetration depth is preferably configured such that it can be set at given levels. At least in the above given levels, the maximum distance between the individual levels is appr. 0.4 mm and the minimum distance is appr. 0.2 mm, preferably 0.3 mm. This range can, of course, also exceed the maximum values to allow deeper penetration, e.g. to account for the relatively small amount of subjects where the above mentioned small penetration depth does not provide a sufficient amount of blood (e.g. due to an excessively thick horn layer). For an exact adjustment of the penetration depth, it is also important to have such a precise positioning of the blade in its holder that it is possible to reproduce the position of the blade end in direction to the pricking movement relative to the blade holder when several blades are successively mounted to the blade holder.

Owing to the advantageous properties of the device in accordance with the invention of displacing/compressing the tissue only very little before penetration, it is possible to achieve a very good reproducibility of the cutting depth which is significantly improved (<+/−0.1 mm) over presently available systems. Due to these very good penetration properties of the device of the invention, individual variation with respect to the skin turgor and/or skin density are now only of secondary importance. This is accomplished in that the tissue opposite the blade is not compressed upon first contact with the forwardly propelled blade; instead, the penetration/cutting does not begin until the blade arrives on the skin.

Figure 4A:
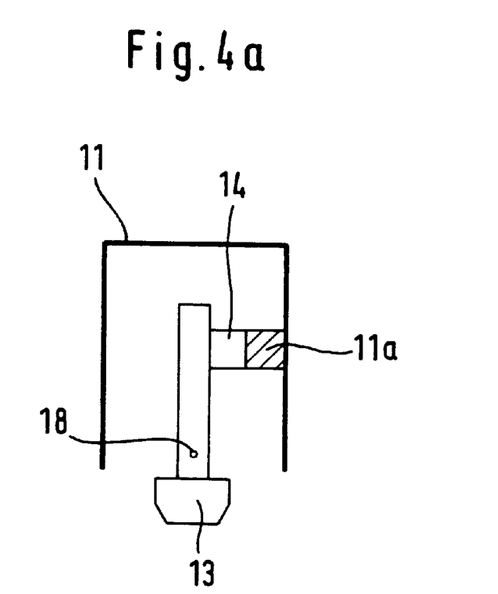

FIG. 4a shows an embodiment where the inner cover (11) is shown together with a configuration of oscillator, bar and blade which is slightly modified with respect to FIG. 4. The piezo crystal (14) and the blade (13) are disposed on different sides with respect to axis (18). By this configuration an oscillation of the blade is being accomplished in the way of a chopping-blade. This type of movement has a comparent parallel to the cutting edge as well as a component vertical thereto. An oscillation of the bar around the axis creates a movement of the blade on a part of a circle.

Figure 11:
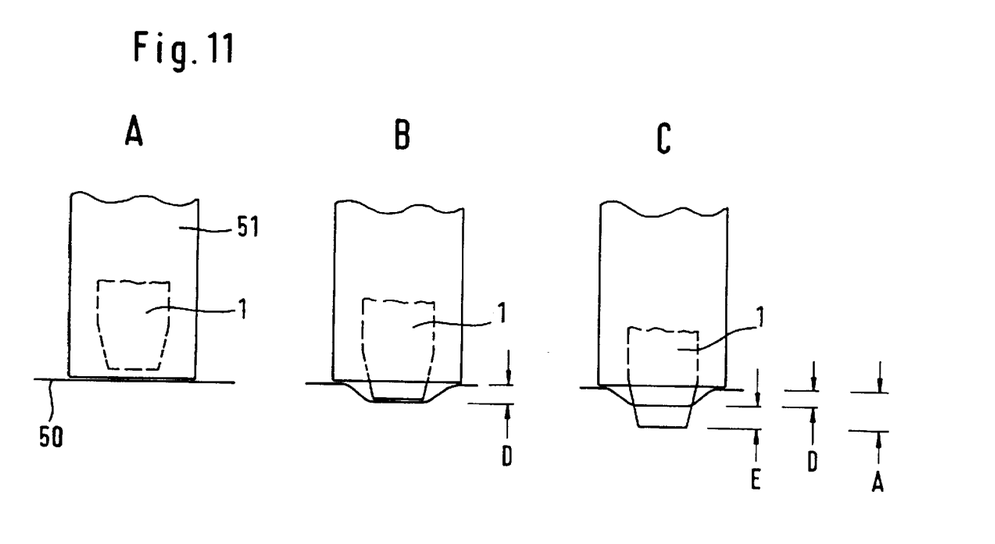
FIG. 11: Representation of the interaction between projection depth (A), deformation (D) and penetration depth (E)

FIG. 11 shows the interaction between the width at which the lancet projects from the cutting device and the penetration depth of the tissue. FIG. 11A shows the initial position of the system where the blade (1) is completely located inside the housing (51) and the housing is pressed onto a part of the skin (50). FIG. 11B shows a condition where the blade displaces the skin without cutting it. Deformation of the skin is identified as (D). FIG. 11C shows a condition where the blade has already cut open the skin. The depth (A) at which the blade projects out of the housing results in a deformation (D) and a penetration depth (E) in the tissue. Deformation (D) can be subject to great deviation within one individual and between different individuals so that the penetration depth can also greatly vary while the projection depth is constant; a fact which is not desired. In devices according to the present invention, the deformation (D) is very small due to the reasons listed above; the deviations of (D) are, hence, also very small. With a defined projection depth (A) the penetration depth (E) into the skin can, hence, be exactly predetermined.

Easy procedures allow the user to precisely set the desired penetration depth. The adjusting range preferably covers unusually deep penetration levels between 0.5 and 2.0 mm, with a range between 0.7 mm and 1.3 mm being of particular importance. The amount of blood necessary for an analysis usually ranges between 1 and 50 $\mu l$, more frequently between 5 and 30 $\mu l$; as the invention has shown, this amount can already be obtained for the majority of individuals at penetration levels where pain is significantly reduced, provided the penetration level can be easily reproduced at a certain, identical setting of the instrument. With an identical setting of the cutting device given, the depth of the cut generated in successive cutting procedures should deviate by less than 0.15 mm, preferably 0.1 mm and particularly preferred 0.05 mm.

The Eccentric Disc-Operated Blood Lancet

FIG. 5A shows a blood lancet where the bar (12) holding the blade (13) is mounted to a weight (41). The weight (41) is located inside an inner cover (23) which in turn is located moveably inside the outer cover (10). The bar (12) which is rigidly connected to the weight (41), e.g. in glued or screwed connection, runs across the weight (41). In the bar (12) there is integrated a piezo element (14) which causes the bar (12) and the blade (13) to oscillate. An enlargement (42) surrounding the opening where the blade emerges can be advantageously provided at the contact surface (16) of the device which is pressed onto the skin. Purpose of this enlargement is to put the part of the skin to be cut open under tension and fix it in position. It has proven to be advantageous if this enlargement (42) projects past the contact surface (16) by 0.2 to 0.3 mm.

Figure 5:
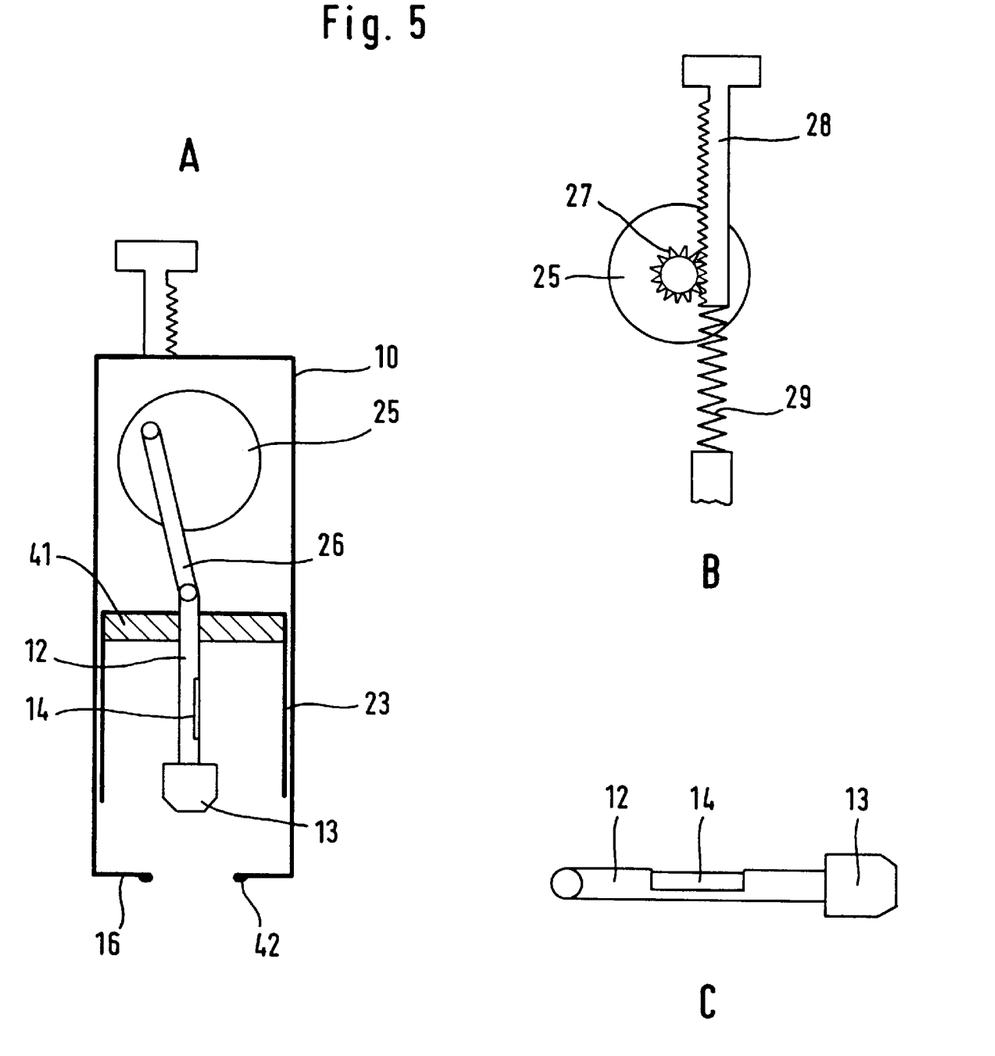
FIG. 5: Blood lancet with an eccentric disk as a propelling mechanism

FIG. 5A also shows an advantageous drive unit for moving the blade into the tissue. This drive unit features an eccentric disk (25) to which a lever (26) is mounted via an axis; another axis connects said lever in turn to the bar (12). FIG. 5B is a rear view of the eccentric disk. On this side said disk has a toothed wheel (27) which is driven via a toothed rod (28). It is an advantage of the device shown in FIG. 5 that when the user presses down the toothed rod (28) the blade is lowered into the tissue and again retracted. Since the user must execute only one single movement, the handling of the device is further facilitated. A spring element (29) can be provided to retract the toothed rod back into its original position. When the tooth rod is pressed down, the spring element is compressed to then move the toothed rod back into its original position. It can also be advantageous to provide some idle for the toothed wheel (27) so that the eccentric disk (25) does not rotate and the blade is not lowered again into the tissue when the toothed rod is retracted into its original position.

FIG. 5C shows the rod (12) with an integrated piezo element (14). The piezo element is configured such that when en electric alternating voltage is applied, it carries out changes in length along its longitudinal axis. These length changes then causes the lever to be bent as is known analogously from bimetallic strips. Mechanical oscillation of the bar (12) can be generated by applying electrical signals having a suitable frequency.

The Blade Types

Figure 6:
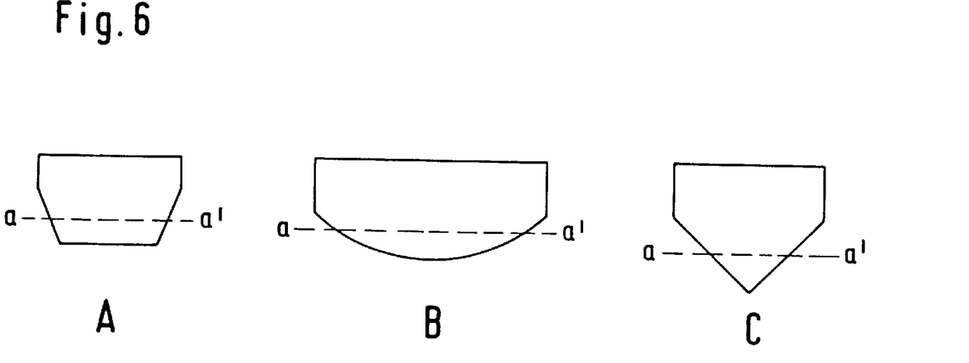
FIG. 6: Blade types
Figure 7:
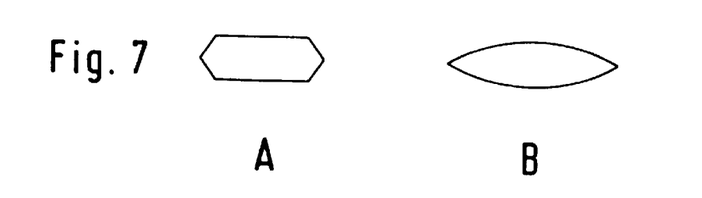
FIG. 7: Cross sections of blades

FIG. 6 shows three embodiments of blades which are preferred in accordance with the invention. FIG. 6A shows a trapezoidal blade with a straight cutting edge. FIG. 6B shows a blade as used in chopping knives while the blade shown in FIG. 6C has a pointed tip. Each of these 3 blade types can have different cross sections. FIG. 7 shows two possible cross sections A and B taken along section line aa' Each of the blades shown in FIGS. 6A through 6C could have one these cross sections. A section line is indicated in FIGS. 6A to 6C to further illustrate this.

The basic shapes of the blades include trapezoids, circles, semi-circles, squares, polygons, pointed tips or chopping blade-type blades. The following taper options are possible:
circumferential ground
facet ground and
ground on both sides The Second Embodiment (Mücke)

The invention also encompasses an embodiment where the blade is made to oscillate perpendicularly to the tissue surface. In this embodiment, owing to the oscillating movement the microscopic movements of the blade and the movements for introducing the blade into the tissue run essentially parallel. In this embodiment it is also advantageous to employ pointed blades and blades with several edges. The latter type can also be achieved with facet grinding.

With this type of device there can be used pin pointed needles which preferably have a facet ground.

The "Mücke"-type device preferably uses a rigid coupling between oscillator and blade which avoids a lateral movement or oscillation of the blade and employs a vertical oscillation with respect to the tissue surface. The oscillation amplitude vertical to the skin surface is set to be smaller than 300 μm, preferably smaller than 100 μm and particularly preferred smaller as 50 μm. For example mechanical oscillators, electrodynamic transformers and piezo elements can be employed as oscillators.

Schematic Representation

Figure 8:
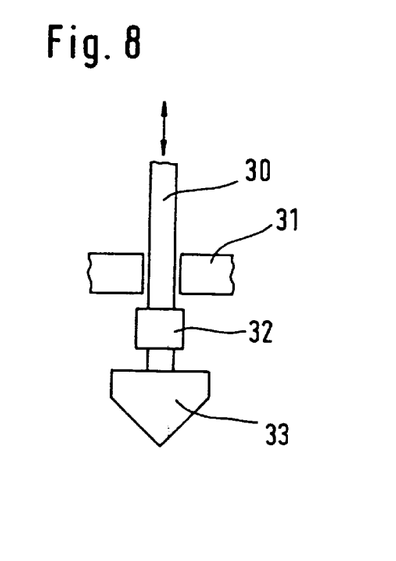
FIG. 8: Principal representation of a Mücke-type blood lancet

FIG. 8 is a schematic representation showing the implementation of this second embodiment. Bar (30) is movable disposed on a sleeve (31). A piezo crystal (32) to transfer oscillations to blade (33) is disposed on bar (30). In this embodiment, the piezo crystal is arranged such that the oscillations generate a movement of the blade (33) in longitudinal direction of the bar in accordance with the double-arrow displayed above the bar. It is of importance that the weight of the oscillating pieces (bar and blade) is small compared to the mass disposed on the other side with respect to the oscillator (which means on side of the bar). In order to carry out a tissue section, the piezo crystal (32) is first made to oscillate; the blade is then lowered into the tissue by moving bar (30). After generating a sufficiently large cut, the bar (30) is moved in opposite direction and the blade (33) is pulled back out of the tissue. Pointed tips have proven well for this embodiment. Especially advantageous are flat blades with cross sections as shown in FIGS. 7A and 7B. Experiments have also shown that the oscillation frequency of the blade transverse to the tissue surface should be above 100 Hz to minimize pain sensation during cutting. By increasing the frequency to above 500 Hz, pain sensation can be further reduced. The amplitude of the oscillating movement should for the same reason be below 100 μm, preferably below 50 μm.

The oscillation of blade (33) necessary for proper operation of the device is achieved with the aid of a suitable geometric arrangement of the masses which generates a so-called resonance step-up of the amplitude.

The schematic representation of the apparatus shown in FIG. 8 can be combined, for example, with the driving mechanisms for moving the blade transversely to the tissue surface as described in FIGS. 4 and 5.

The Manual Pricking Aid

Figure 9:
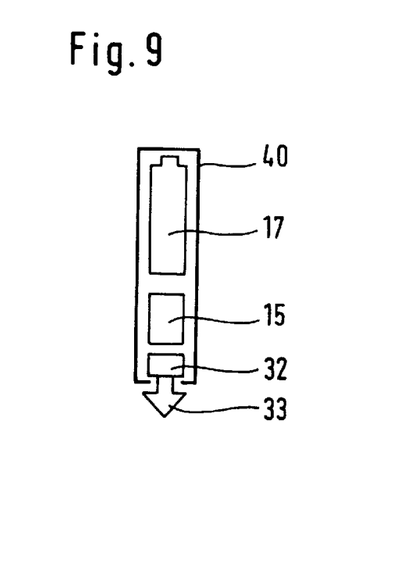
FIG. 9: Manually operated blood lancet of the Mücke-type

FIG. 9 shows a particularly simple embodiment where a battery-operated electronic oscillation generator (15) is located within a housing (40). This oscillation generator (15) causes the piezo crystal (32) to oscillate. In this embodiment the blade is directly coupled to the piezo crystal. The user moves the blade (33) to the tissue to be cut open and carries out a cut at the desired depth.

List of Reference Numerals
(1) blade
(2) cutting edge
(10) outer cover
(11) inner cover
(11a) connecting piece
(12) bar
(13) blade
(14) piezo crystal
(15) electronic oscillation generator
(16) contact surface
(17) battery
(18) axis
(19) weight
(20) spring element
(21) guide with recess
(22) lever
(23) guide element
(24) rubber
(25) eccentric disk
(26) lever rod
(27) toothed wheel
(28) toothed rod
(29) spring element
(30) bar
(31) sleeve
(32) piezo crystal
(33) blade
(40) housing
(41) weight
(42) enlargement

What is claimed is:

1. A device for obtaining small blood samples from humans or animals in an almost pain-free manner, the device comprising:
    a blade having a cutting edge with a length of less than 10 mm; and
    an oscillator means for making the blade oscillate at a frequency along an axis that is substantially parallel to the cutting edge.

2. The device according to claim 1 further comprising:
    a housing in which the blade and the oscillator means are disposed; and
    a contact surface for establishing contact with a skin surface, said contact surface having an opening which is large enough for the blade to extend therethrough while oscillating.

3. The device according to claim 2 wherein the skin contact surface includes an enlargement running around an edge of the opening which puts the skin surface under tension and fixes the skin surface in position.

4. The device according to claim 3 wherein the enlargement projects beyond the contact surface by 0.2 to 0.3 mm.

5. This device according to claim 2 wherein the blade is moveable generally perpendicualr to the cutting edge so that in a first position the cutting edge is disposed inside the housing and in a second position the cutting edge projects beyond the contact surface.

6. The device according to claim 2 wherein the blade is fixed to the housing in a position perpendicular to the skin surface and the skin contact surface is provided on a sleeve which is mounted on an adjustable spring stop such that a maximum penetration depth of the blade into the skin surface is set.

7. The device according to claim 2 further comprising setting means for setting a maximum length by which the blade can project past the contact surface during cutting wherein the maximum length set varies from a minimum limit of 200 μm up to a maximum limit of 2500 μm.

8. The device according to claim 1, wherein the oscillator means is coupled to the blade via a bar.

9. The device according to claim 8 wherein the oscillator is a piezo element integrated into the bar and changes in the length of the piezo element with respect to a longitudinal axis of the bar are created by an alternating voltage applied to the piezo element.

10. The device according to claim 8 wherein the bar and the blade form an exchangeable mechanical unit.

11. The device according to claim 10 wherein the bar and the blade are made from the same material and form a one piece unit.

12. The device according to claim 1 wherein the cutting edge of the blade has a length of 0.2 to 2.0 mm.

13. The device according to claim 1 wherein the frequency of the oscillation is above 500 Hz.

14. The device according to claim 1 wherein the amplitude of the oscillation is below 500 μm.

15. The device according to claim 1 wherein a propelling mechanism moves the blade perpendicularly to the cutting edge.

16. The device according to claim 15 wherein the propelling mechanism moves the blade perpendicularly to the cutting edge at a speed of less than 2 km/hr.

17. The device according to claim 1 wherein the blade is attached to a spring-loaded element and upon releasing a spring tension the blade is moved perpendicularly to the cutting edge.

18. The device according to claim 1 wherein the blade has a basic shape which is a trapezoid, circle, semi-circle, square, polygon, pointed tip or chopping knife shape.

19. The device according to claim 1 wherein the blade is circumferential ground, facet ground or ground on both sides.

20. The device according to claim 1 wherein the oscillator means further comprise a piezo crystal, an ultraceramics element, an electrodynamic transformer, or a mechanically excited element as an oscillating element and said oscillating element is activated via an electronic or mechanical oscillation generator.

21. The device according to claim 1 wherein the oscillator means is a mechanical oscillator.

22. The device according to claim 1 wherein the blade is made from a plastic which can be processed in an injection molding process.

23. The device according to claim 1 further comprising a friction reducing substance coating the blade to reduce friction between the blade and tissue.

24. A method of cutting skin tissue for obtaining blood samples of less than 50 μl from humans or animals in an almost pain-free manner, the method comprising the steps of:

providing a blade having a cutting edge of less than 10 mm in length and oscillating the blade at an oscillation frequency in at least one direction which is substantially parallel to the cutting edge;

moving the oscillating blade perpendicularly toward and into tissue to be cut open; and thereafter retracting the blade from the tissue.

25. The method according to claim 24 wherein the oscillation movement comprises a component parallel to the cutting edge as well as a component perpendicular thereto.

26. The method according to claim 25 wherein the oscillating blade defines a segment of a circle during oscillation.

27. The method according to claim 26 wherein the oscillation frequency is above 500 Hz.

28. The method according to claim 24 wherein the perpendicular movement of the blade into the tissue and the retraction of the blade from the tissue are carried out manually.

29. The method according to claim 24 wherein the steps of moving and retracting the blade comprise moving the blade at a speed of less than 2 km/h.

30. The method according to claim 24 wherein the blade is retracted from the tissue along a path that runs in the cutting channel.

31. The method according to claim 24 wherein the step of moving the blade toward and into the tissue comprises guiding the blade to a depth of less than 2500 μm under the surface of the tissue.

* * * * *